(12) United States Patent
Williams et al.

(10) Patent No.: US 6,309,535 B1
(45) Date of Patent: Oct. 30, 2001

(54) ELECTRODES AND THEIR USE IN ASSAYS

(75) Inventors: Stephen Charles Williams, Half Moon Bay, CA (US); Bernadette Yon-Hin; Neil Blair, both of Cambridge (GB)

(73) Assignee: Cambridge Sensors Limited, Cambridge (GB)

( * ) Notice: Subject to any disclaimer, the term of this patent is extended or adjusted under 35 U.S.C. 154(b) by 0 days.

(21) Appl. No.: 09/297,717
(22) PCT Filed: Nov. 6, 1997
(86) PCT No.: PCT/GB97/03046
§ 371 Date: Jul. 19, 1999
§ 102(e) Date: Jul. 19, 1999
(87) PCT Pub. No.: WO98/20331
PCT Pub. Date: May 14, 1998

(30) Foreign Application Priority Data

Nov. 7, 1996 (GB) .................................... 9623272
Jun. 18, 1997 (GB) .................................... 9712691

(51) Int. Cl.$^7$ .................................................. G01N 27/26
(52) U.S. Cl. .................................. 205/777.5; 205/794.5; 204/403; 204/294
(58) Field of Search ............................... 205/794.5, 777.5; 204/403, 294

(56) References Cited

U.S. PATENT DOCUMENTS

| 4,933,062 | | 6/1990 | Shaw et al. ........................ 204/291 |
| 5,231,028 | * | 7/1993 | Mullen .............................. 435/287.9 |
| 5,429,735 | | 7/1995 | Johnson et al. ..................... 204/403 |
| 5,795,453 | * | 8/1998 | Gilmartin ........................... 204/403 |

FOREIGN PATENT DOCUMENTS

| 3932247 A1 | 9/1989 | (DE) | ............... G01N/27/30 |
| 0 244 626 A1 | 3/1987 | (EP) | ............... B01D/13/02 |
| 2191003 | 12/1987 | (GB) | ............... G01N/27/30 |
| WO 88/08447 | 11/1988 | (WO) | ............... C12M/1/40 |

OTHER PUBLICATIONS

"Metal–Dispersed Carbon Paste Electrodes" by J. Wang, N. Naser, L. Angnes. H. Wu, and L. Chen; 266b Analytical Chemistry 64(1992) Jun. 1, No. 11, Washington, DC, US.

* cited by examiner

*Primary Examiner*—T. Tung
*Assistant Examiner*—Alex Noguerola

(57) ABSTRACT

An electrode comprises a non-conductive substrate and a conductive layer comprising, in a bonded matrix, graphite particles coated with a noble metal, and carbon particles, wherein the graphite particles are up to 20 μm is size and have a surface area of 1–50 m$^2$/g. This electrode is capable of measuring low levels of analyte, e.g. glucose in sweat when convined with a layer containing glucose oxidase.

20 Claims, No Drawings

ELECTRODES AND THEIR USE IN ASSAYS

FIELD OF THE INVENTION

This invention relates to electrodes and their use in assays, and in particular to the detection and quantification of analytes that are present only at low levels.

BACKGROUND OF THE INVENTION

Electrodes have been produced by deposition of conductive ink materials onto solid substrates. Such devices may comprise a solid layer of a precious metal, e.g. gold or platinum, on a ceramic substrate. They may be produced by, for example, thick film deposition (TFD) of an ink material loaded with finely-divided particles of the metal; drying the ink layer at extreme temperatures (usually in excess of 500° C.) removes all ink components such as binders and solvents, and fuses together the particles of precious metal, to form a continuous film of metal on the substrate.

The performance of such devices as electrode materials very closely approximates to that of ideal materials, i.e. solid, machined pure metal electrodes of (say) gold and platinum characterised by high conductivity, high sensitivity to the analyte of interest, low noise levels, and a response to the analyte which is relatively independent of temperature. However, such devices are expensive to produce, since the ink materials must have extremely high metal loadings, and require expensive high temperature drying/curing facilities.

Alternative electrode materials have been described, which are fabricated by TFD of an ink material consisting of finely-divided noble metal particles, intimately mixed with or deposited on carbon, a resin binder material and, if required, a solvent. Such devices are considerably less expensive than those described above, since the ink materials contain much lower levels of noble metal and are fabricated by low temperature curing of the ink material; the carbon content of the ink is designed to compensate for the loss in conductivity that results from reduction of the noble metal content.

Such carbon-based devices are described in, for example, GB-A-2191003. They suffer from three major problems. Firstly, the noble metavcarbon mix is highly heterogeneous, so that products suffer from very poor precision due to the non-uniform dispersion of the noble metal in the ink material. Secondly, there are high background currents during analysis (cf noise), resulting from high surface areas of the carbon components; non-faradaic components, i.e. double layer charging currents. are a direct function of the carbon particle surface area. Thirdly, the temperature dependency of the background current increases with increasing temperature; this is usually a function of the flexible nature of the polymer binder, which essentially softens with increasing temperature, thus changing the surface topography of the electrode.

Diabetes is the most common endocrine disease, and has major deleterious health consequences for the sufferers. Disease morbidity may be decreased by a program of blood glucose monitoring in which patients use samples of blood to monitor their blood glucose levels and adjust diets, drugs and insulin therapy according to the level of blood glucose. In extreme cases, such monitoring may be used to avoid hypoglycemic attacks which may cause coma and subsequent death. However, blood for analysis is obtained either by a fingerstick or venous sample, which causes patient pain and discomfort. Sweat-collecting devices are known. These are usually skin patches made of a hydrogel containing permeation enhancers. The collected sweat or exudate is either placed in water to allow the glucose to diffuse out of the hydrogel and then be analysed or the skin patch is allowed to concentrate the sweat in the patch by driving off the collected water and a specific binding partner in the patch is used to present a visual indication of its presence in the patch. These methods are both qualitative. In addition, the patient has to carry out several manipulations which would be particularly difficult if the patient is ill or entering hypoglycemic coma.

GB-A-2191003 (see above) discloses that an enzyme such as glucose oxidase should be adsorbed or immobilised on the resin-bonded carbon or graphite particles of an electrode. For example, enzyme is held within the pores of the oxygen-permeable resin-bonded layer.

WO-A-97028 11 discloses a hydrogel patch containing glucose oxidase. This can be used with a standard electrode, as a glucose sensor.

SUMMARY OF THE INVENTION

According to the present invention, an electrode comprises a conductive layer, positioned by thick film printing, on a non-conducting plastic substrate. The conductive layer comprises graphite particles (size up to 20 $\mu$m; surface area 1–50 $m^2/g$) uniformly coated with a noble metal such as platinum, and non-coated andlor platinum-coated carbon particles, held sufficiently close together to facilitate electrical contact between the particles, by a polymer binder.

Electrodes of the invention allow the amperometric detection of electroactive analyte species at low concentrations, with improved signal-to-noise ratios resulting from the use of low surface area graphitic supports. the improved homogeneity of the metal coating on the surface of the graphite particle leads to improved electrode-to-electrode precision, and the cross-linking of the polymer binder reduces the sensitivity of the electrode response to fluctuations in temperature.

DESCRIPTION OF THE INVENTION

In producing products of the invention, the essential components may be deposited as a single electrode, a micro-electrode or as a microelectrode array. The electrode may be used in conjunction with referencelcounter electrodes deposited on the same substrate. For example, an electrode device may be produced by depositing a noble metal-modified graphite, carbon and polymer binder-containing, conducting layer on a non-conducting substrate, and depositing a second conducting layer comprising silver/silver chloride, to function as a reference/counter electrode, adjacent to the first layer.

The non-conducting substrate material may be a polyester sheet material, or made of polycarbonate, polyvinyl chloride, high density polypropylene or low density polypropylene. In a preferred embodiment, a polyester sheet material is heat stabilised prior to application of the conducting layers, to confer dimensional stability.

For the conducting layer, the noble metal is, for example, platinum, rhodium, palladium, iridium, ruthenium or osmium. The graphite component has an average particle size of less than 20 $\mu$m and a typical surface area less than 50 $m^2/g$, and is inherently conductive, it may be derived from either natural sources or produced synthetically. The noble metal is deposited uniformly onto the surface of the graphite material, or is uniformly dispersed in colloidal form within the graphite material. Preferably, the amount of the metal is 5–20% w/w with respect to the graphite.

The carbon component has an average particle size less than 1 μm, e.g. 5–70 nm, and a typical surface area of less than 150, e.g. 1–150, m²/g. Like the graphite component, it is also inherently conductive. The polymer binder may be derived from any of the diverse polymer families. It preferably contains chemical fiunctionalities which facilitate covalent cross-linking, such as carboxylate, hydroxyl, amine, thiol, ester, epoxide or amide groups.

The conducting electrode material may be deposited on the non-conducting substrate by a conventional printing process, e.g. thick film printing (also known as screen printing), lithography, letter press printing, vapour deposition, spray coating, ink jet printing, laser jet printing, roller coating or vacuum deposition.

Following deposition of the conductive electrode material, the polymer binder may be stabilised or cured by a number of conventional processes, such as forced air drying, forced air drying at elevated temperatures, infra-red irradiation, ultraviolet irradiation, ion beam irradiation or gamma irradiation. All of these processes result to varying degrees in the cross-linking of individual molecules of the polymer binder. The use of ultraviolet radiation requires the inclusion of a photo-sensitising reagent in the conductive electrode material, to initiate the polymer cross-linking reaction.

In an alternative embodiment, the cross-linked layer is deposited from an ink having a high content of graphite, carbon, cross-linker and binder. The graphite, carbon and polymer may be essentially as described above. Before or after cross-linking, this layer is modified with a noble metal, e.g. by electrochemical deposition.

Electrodes of the invention have several characteristics that make their use desirable for the measurement of low concentrations of analytes. For example, the electrodes exhibit low background noise electrochemistry which is of particular importance in the measurement of low levels of electrical current.

The presence of a noble metal in the conductive layer facilitates the oxidation/reduction of analyte species at lower potentials compared to the use of graphite/carbon alone. The uniformity of the dispersion of the noble metal affords a high level of electrode-to-electrode precision in terms of response. In addition, the temperature-dependency of the response of the electrodes to analyte is reduced by chemical cross-linking of the polymer binder.

Electrodes of the invention may be used for the analysis of analytes/species which can be directly oxidised or reduced by the removal or addition of electrons at an electrode. They may also be used to detect analytes/species which can be readily converted by an enzyme, to a product which can be directly oxidised or reduced by the removal or addition of electrons at an electrode. It is preferred that a product of the invention includes such an enzyme, e.g. glucose oxidase.

Preferably, the enzyme is maintained on the electrode in a layer that is separate from but in intimate contact with the conducting layer. For example, a hydrogel; sol-gel or porous layer containing the enzyme is applied onto the conducting layer, by printing. Alternatively, a gel is used for contacting the skin, but the enzyme is held in an intermediate layer, e.g. a microporous membrane; this may help to keep the enzyme dry, and therefore stable, and also enhance absorption of sweat. A gel may include sweat or permeability enhancers.

A preferred embodiment of the present invention is a device which, when placed in direct contact with the skin, is capable of inducing permeation or sweating of a subject. Its use then comprises collecting the analyte of interest in close proximity to the sensing electrodes and measuring amperometrically low levels of the active analyte. One conducting track is used to thermally induce sweating and hence the transport of the active analyte. In another configuration, the device may include electrodes to induce sweating by iontophoresis. The sensing electrodes consist of a working electrode sensitive to low concentration of analyte and a reference/counter electrode. The device is sensitive to micromolar glucose concentrations. The device may be reused in siii; the detection system does not require the sample to be collected first in a separate membrane or device, before analysis. In this manner, a rapid analysis of the level of glucose diffusing through the skin may be made without a large amount of patient manipulation or replacement of membranes.

More specifically, such a device can be used for measuring glucose, when placed in direct contact with the skin. The electrode device comprises printed electrodes in contact with a gel (although alternative systems may also be used, as described above), a conducting layer of silver or carbon capable of thermally inducing sweating, a second conducting layer consisting of noble metal in a carbon, graphite and polymer binder to function as the working electrode, and a third conducting layer of silver/silver chloride to function as a reference/counter electrode.

The conducting layer of silver is used as a heating circuit, to induce sweating in the patient. The sweat is collected in the gel next to the skin and, in order to induce the passage of glucose through the skin, the device may optionally include sweat or permeability enhancers in the gel layer. Additionally, the gel layer contains glucose oxidase enzyme to convert glucose to hydrogen peroxide. The presence of a noble metal in the conductive layer facilitates the oxidation of hydrogen peroxide.

In use, the device is positioned directly against the epithelial membrane so that intimate contact is made between the device surface and the skin. After a fixed period of time, glucose diffuses out through the skin into the gel via the use of the heating circuit inducing sweating or the activity of permeation enhancers present in the gel. Glucose accumulated in the gel layer is oxidised by glucose oxidase and hydrogen peroxide is formed.

When a suitable potential, e.g. 500 mV, is applied between the working electrode and the referencelcounter electrode, a current reading is obtained as a result of the oxidation of hydrogen peroxide. The current measured is directly proportional to the concentration of glucose in the patient.

The following Example illustrates the invention.

EXAMPLE

A conductive ink material was deposited on a nonconducting 125 μm thick polyester sheet, by screen printing. The ink material comprised a triple roll-milled mixture of 32 g of 5% platinum coated-graphite particles (average particle size 1 μm; surface area 15 m²/g), 0.98 g carbon particles (average particle size 40 nm; surface area 100 m²/g), 35 g of a 30% vinyl chloride/vinyl acetate copolymer binder in 52 g of an organic solvent (Polyspeed from Coates), 15 phr of a bifunctional cross-linking agent (hexamethoxymethylmelamine) and 1% acid catalyst. After deposition of the conductive ink, solvents were removed in a forced air oven. Heating to 140° C. initiated the cross-linking of the polymer binder by the bifunctional amine.

A silver/silver chloride, screen-printed reference or reference/counter electrode was located adjacent to the conductive carbon layer on the polyester support. A conductive carbon counter-electrode was located near the working and reference electrodes. A silver conductive track was applied around the working, reference and counter electrodes, to provide a means of electrically heating the device. A glucose oxidase-containing hydrophilic polymer layer or hydrogel was then deposited over the electrodes.

The device is used by applying the polymer or hydrogel to the skin of a subject. On electrical heating of the device, sweating is induced. The sweat diffuses into the polymer or hydrogel where it reacts with glucose oxidase to produce hydrogen peroxide. When a potential is applied across the conductive Pt/carbon electrode and the silver/silver chloride electrode, the electrode device can be used for the measurement of hydrogen peroxide using chronoamperometry. The sensitivity of the device to hydrogen peroxide is 50–100 nA/$\mu$M.

The device gives very low background responses in buffer (7 nA) and in hydrogel (22 nA), at potentials of 0.6 and 0.5V respectively. The effect of temperature on the background signal is also low.

What is claimed is:

1. An electrode comprising a non-conductive substrate and a conductive layer positioned on the non-conductive substrate, the conductive layer comprising, in a bonded matrix, graphite particles coated with a noble metal, and uncoated carbon particles, wherein the graphite particles are up to 20 $\mu$m in size and have a surface area of 1–50 m$^2$/g and the carbon particles have an average size of less than 1 $\mu$m.

2. An electrode according to claim 1, wherein the carbon particles are 5–70 nm in size, and have a surface area of less than 150 m$^2$/g.

3. A electrode according to claim 2, wherein the noble metal is platinum.

4. An electrode according to claim 3, wherein the graphite particles are coated with 5–20% w/w of the metal.

5. An electrode according to claim 4, wherein the matrix is a cross-linked polymer.

6. An electrode according to claim 5, which additionally comprises a further layer, on the conductive layer, including an enzyme.

7. An electrode according to claim 1, wherein the noble metal is platinum.

8. An electrode according to claim 7, Wherein the graphite particles are coated with 5–20% w/w of the metal.

9. An electrode according to claim 8, wherein the matrix is a cross-linked polymer.

10. An electrode according to claim 9, which additionally comprises a further layer, on the conductive layer, including an enzyme.

11. An electrode according to claim 1, wherein the graphite particles are coated with 5–20% w/w of the metal.

12. An electrode according to claim 11, wherein the matrix is a cross-linked polymer.

13. An electrode according to claimn 12, which additionally comprises a further layer, on the conductive layer, including an enzyme.

14. An electrode according to claim 1, wherein the matrix is a cross-linked polymer.

15. An electrode according to claim 14, which additionally comprises a further layer, on the conductive layer, including an enzyme.

16. An electrode according to claim 1, which additionally comprises a further layer, on the conductive layer, including an enzyme.

17. An electrode according to claim 16, which additionally comprises a separate conducting layer, capable of being heated.

18. An electrode according to claim 17, wherein the enzyme is glucose oxidase.

19. An electrode according to claim 6, wherein the enzyme is glucose oxidase.

20. A method of amperometrically detecting glucose in a host comprising contacting the skin of the host with an electrode according to claim 19, collecting sweat from the host in the further layer including the glucose oxidase enzyme, permitting the sweat to react with the glucose oxidase enzyme to produce hydrogen peroxide, and amperometrically measuring the hydrogen peroxide produced as a measure of glucose in the host.

* * * * *